United States Patent [19]

Ehrlich et al.

[11] Patent Number: 5,659,037

[45] Date of Patent: Aug. 19, 1997

[54] PROCESS FOR PREPARING CHIRAL TETRACYCLIC DOPAMINERGIC COMPOUNDS

[75] Inventors: Paul P. Ehrlich, Libertyville; Michael R. Michaelides, Gurnee; Maureen A. McLaughlin, Chicago; Chi-Nung Hsaio, Libertyville, all of Ill.

[73] Assignee: Abbott Laboratories, Abbott Park, Ill.

[21] Appl. No.: 463,326

[22] Filed: Jun. 5, 1995

Related U.S. Application Data

[63] Continuation-in-part of Ser. No. 292,677, Aug. 18, 1994.

[51] Int. Cl.$^6$ .................................................. C07D 215/20
[52] U.S. Cl. ........................... 546/62; 546/61; 564/167; 549/77; 549/75; 549/496
[58] Field of Search ........................................ 546/61, 62

[56] References Cited

U.S. PATENT DOCUMENTS

| 3,131,191 | 4/1964 | Douglas | 546/76 |
| 4,120,964 | 10/1978 | Hartenstein | 546/76 |
| 5,047,536 | 9/1991 | Nichols | 546/61 |
| 5,420,134 | 5/1995 | Nichols | 546/48 |

FOREIGN PATENT DOCUMENTS

| 92-04356 | 3/1992 | WIPO | 546/61 |
| WO 93/24462 | 12/1993 | WIPO . | |
| WO 94/22858 | 3/1994 | WIPO . | |

OTHER PUBLICATIONS

Nordlander et al. J. Org Chem. vol. 50 pp. 3619–3622 (1985).

Angelastro et al J Org Chem vol. 54 pp. 3913–3916 (1989).

Cupps et al J. Org. Chem. vol. 50 pp. 3972–3979 (1985).

Moyer et al J Org Chem vol. 51 pp. 5106–5110 (1986).

Brewster, J. Med. Chem. vol. 33, pp. 1756–1774 (1990).

Brewster, et al., "trans–10,11–Dihydroxy–5,6,6I,7,8, 12b–Hexahydrobenzo[a]phenanthridine: A Highly Potent Selective Dopamine $D_1$ Full Agonist", *J. Med. Chem.*, 33;1756–64 (1990).

Knoerzer, et al., "Dopaminergic Benzo[a]phenanthridines: Resolution and Pharmacological Evaluation of the Enantiomers of Dihydrexidine, the Full Efficacy $D_1$ Dopamine Receptor Agonist", *J. Med. Chem.*, 37:2453–60 (1994).

*Primary Examiner*—Donald G. Daus
*Attorney, Agent, or Firm*—Monte R. Browder

[57] ABSTRACT

A process for preparing a chiral tetracyclic compound of formula:

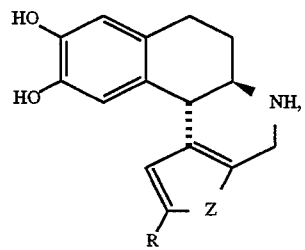

wherein R is hydrogen or a $C_1$–$C_6$-alkyl group and Z is oxygen, sulfur or —CH=CH—, the compounds having uses as dopamine agonists. The process involves reacting a chiral starting material and subsequent chiral intermediates in a series of chirality-preserving synthetic reactions.

8 Claims, No Drawings

PROCESS FOR PREPARING CHIRAL TETRACYCLIC DOPAMINERGIC COMPOUNDS

This application is a continuation-in-part of U.S. application Ser. No. 08/292,677, filed Aug. 18, 1994.

TECHNICAL FIELD

This invention relates to a process for preparing chiral tetracyclic compounds having use as dopamine agonists.

BACKGROUND OF THE INVENTION

The central nervous system (CNS) relies in part upon dopaminergic neurotransmission for its full and efficient operation. Therefore, agents that act as ligands at dopamine receptors are likely to have CNS activity. Use of such agents may be of great value in CNS research or, potentially, as therapeutic agents.

The significance of certain tetracyclic compounds as dopamine agonists has been described by M. R. Michaelides et al. in WO94/22858 (corresponding to U.S. patent application Ser. No. 08/209,982, filed Mar. 17, 1994, which is incorporated herein by reference). In addition, other tetracyclic compounds such as dihydrexidine, a trans-10,11-dihydroxy-5,6,6a,7,8,12b-hexahydrobenzo[a]phenanthridine, and its 2-methyl derivative have been identified as potent and selective dopamine D1 agonists (cf., D. E. Nichols, U.S. Pat. No. 5,047,536, issued Sep. 10, 1991, Nichols, R. B.; Mailman, R. B. WO 93/24462, published Dec. 9, 1993 and Brewster et al, *J. Med. Chem.*, 33:1756–64 (1990)).

Obtaining either of these tetracyclic moieties in chiral form has not been easy, however. Dihydrexidine is known to possess within its fused ring system the trans-configuration of fused rings which corresponds to the structure of the powerful dopamine agonist, 2-amino-6,7-dihydroxy-1,2,3,4-tetrahydronaphthalene (ADTN), which itself possesses greatest activity in its chiral (R)-(+)-isomeric form (see P. Seeman, *Pharmacol. Rev.* 32:2:229 (1980)). Knoerzer et al. (*J. Med. Chem.*, 37:2453–60 (1994)) have now reported the resolution of the pair of chiral isomers of dihydrexidine and confirm that the 6aR,12bS-(+)-isomer is the more active pharmacologically. They also showed that the 6aS,12bR-(−)-isomer is inactive in an adenylate cyclase assay.

The synthesis of dihydrexidine as reported by Nichols and Brewster (cited above) generates the racemic pair of trans-isomers (6aR,12bS and 6aS,12bR) and, therefore, represents an inefficient preparation of the active chiral isomer (50% maximum theoretical yield of the desired isomer). In addition, the chiral products of Michaelides et al (cited above) are also prepared by resolution of the racemate, and therefore their synthesis also has a theoretical maximum 50% efficiency.

We have now found, and the present invention describes, a process for preparing chiral isomers of dihydrexidine and, particularly, of certain other tetracyclic dopaminergic compounds as described above.

This process begins with an improved synthesis of the known chiral starting material ((2R)-4-(3,4-dimethoxyphenyl)-2-((trifluoroacetyl)amino)butyric acid, CAS Reg. No. 97403-65-1, compound (2) in the process described below), and proceeds through a series of chiral intermediates, thus assuring the chiral purity of the final product.

For the synthesis of compound (2), Nordlander et al. (*J. Org. Chem*, 50:3619–3622 (1985)) utilized methylene chloride as the solvent in the initial condensation step, and he reported a 55% yield. This yield could not be obtained in our hands (see Examples 7–9 and Table 2 below), and we have found that the use of nitromethane in place of methylene chloride as the solvent allows for improved and reliable yields.

Literature searches have shown that the intermediates below identified by the numbers 3, 5, 6, and 7 are novel compounds. The ability to maintain chirality within step (b) below was earlier confirmed by T. L. Cupps et al. (*J. Org Chem*50:3972–79 (1985)) and M. R. Angelastro et al. (*J. Org. Chem.*, 54:391 3–16 (1989)), among others, who reported that alpha-amino acids such as phenylalanine, for example, may be converted into the chiral N-methoxy-N-methyl-amides or isoxazolidides thereof.

The subsequent ability to condense chiral amides with organometallic ligands, as in step (c) below, has been reported with various ring systems such as indole (M. P. Moyer et al., *J. Org. Chem.*, 51:5106–10 (1986)), tetrahydropyridines (J. S. Ward et al., *J. Hetero. Chem.* 27:1709–12 (1990)), dimethoxyisocoumarins (C. N. Lewis et al., *Synthesis-Stuttgart*, 11:944–946 (1986)), and substituted thiazoles (J. J. McNally et al., *J. Hetero. Chem.*, 29:247–250 (1992)).

The reduction of chiral alpha-keto amines to the corresponding alpha-hydroxy amines, as in step (d) below, is known. Also known is cyclization and dehydration of suitable alcohol compounds to form ring compounds, as in step (e) below, and the condensation of an amine with an intramolecular carbon atom with the assistance of a suitable leaving group, as in step (f) below.

However, there is nothing in the individual references cited, nor in other literature, taken together with such references, to suggest the process of the present invention.

SUMMARY OF THE INVENTION

The present invention is directed to a process for preparing chiral forms of tetracyclic compounds of the formula:

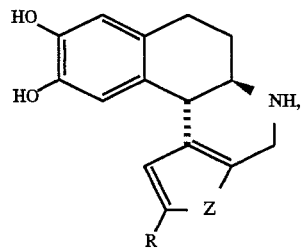

wherein R is hydrogen or a $C_1$–$C_6$-alkyl group and Z is oxygen, sulfur or —CH=CH—, having use as dopamine agonists, by reacting a chiral starting material and subsequent chiral intermediates in a series of chirality-preserving synthetic reactions.

DETAILED DESCRIPTION OF THE INVENTION

This invention relates to a novel process for the preparation of a chiral compound of formula (1).

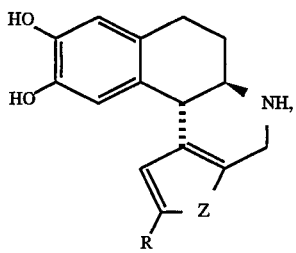

wherein R is hydrogen or a $C_1$–$C_6$-alkyl group, as defined below, and Z is oxygen, sulfur or —CH=CH—, by:

(a) reacting a chiral starting material of formula (2),

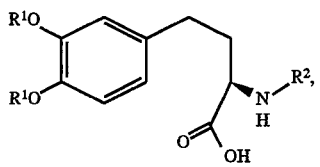

wherein $R^1$ is a catechol-protecting group, as defined below, and $R^2$ is an amino-protecting group, as defined below; with hydroxamide-generating reagents, as defined below, to give the chiral intermediate compound of formula (3),

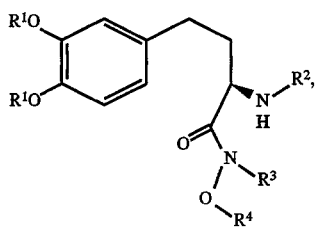

wherein $R^3$ and $R^4$ are each methyl, or $R^3$ and $R^4$ taken together is —$CH_2$—$CH_2$—$CH_2$—, and $R^1$ and $R^2$ are as defined above;

(b) reacting the compound of formula (3) with a nucleophilic reagent of formula (4),

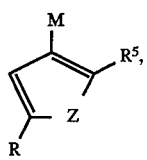

wherein R and Z are as described above, M is an alkali metal or the Grignard (MgX) moiety, and $R^5$ is hydrogen, hydroxymethyl or a hydroxymethyl-equivalent group, as defined below, to form the chiral compound of formula (5),

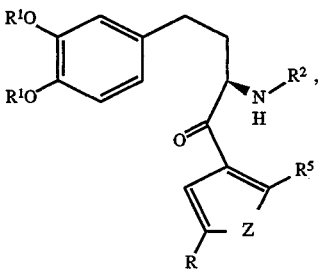

wherein R, $R^1$, $R^2$, $R^5$ and Z are as defined above;
(c) reducing the compound of formula (5) to the chiral compound of formula (6),

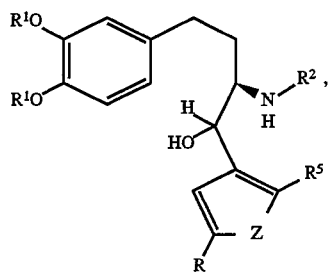

wherein R, $R^1$, $R^2$, $R^5$ and Z are as described above;
(d) cyclizing the compound of formula (6) in the presence of a Lewis acid and a suitable solvent to give a high yield of the chiral trans compound of formula (7),

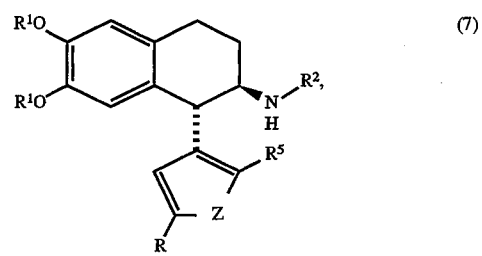

wherein R, $R^1$, $R^2$, $R^5$ and Z are as described above;
(e) removing the $R^2$ and optional hydroxymethyl-equivalent protecting groups and cyclizing the compound of formula (7) under suitable conditions to give the chiral intermediate of formula (8),

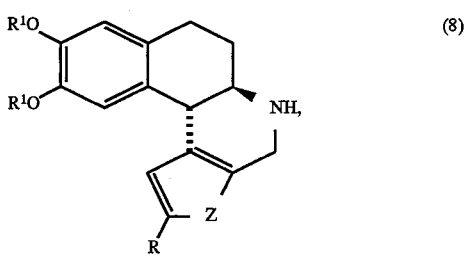

wherein R, $R^1$ and Z are as described above; and finally
(f) removing the catechol-protecting groups, $R^1$, from the compound of formula (8) to give a high yield of the desired product, (1).

One embodiment of the process is that for preparing a chiral compound of formula (1), wherein Z is sulfur, and comprises: steps (a) and (b), as shown above; in step (c) reacting the compound of formula (3) with a nucleophilic reagent of formula (4), wherein Z is sulfur and R, M, and $R^5$ are as described above, to form the chiral compound of formula (5), wherein Z is sulfur; and following with steps (d)–(g), as shown above, to give the desired product.

A preferred embodiment of the process is that for preparing a chiral compound of formula (1), wherein Z is sulfur and R is propyl, and comprises: steps (a) and (b), as shown above; in step (c) reacting the compound of formula (3) with a nucleophilic reagent of formula (4), wherein Z is sulfur, R is propyl, M is a Grignard moiety and $R^5$ is as described above, to form the chiral compound of formula (5), wherein Z is sulfur and R is propyl; and following with steps (d)–(g), as shown above, to give the desired product.

A further preferred embodiment of the process is where the starting compound (2) is prepared by reacting a chiral N-protected-D-aspartic anhydride with a protected catechol in the presence of $AlCl_3$ and with nitromethane as the solvent, followed by reduction of the intermediate thus formed with a ketone reducing reagent, as defined below. This preferred variation provides better yields than known literature methods.

A compound prepared by these more preferred embodiment is trans-(5aR,11 bS)-4,5,5a,6,7,11b-hexahydro-2-propyl-3-thia-5-aza-cyclopent-1-ena[c]-phenanthrene-9,10-diol coupled with a pharmaceutically-acceptable salt.

Another embodiment of the process is that for preparing a chiral compound of formula (1), wherein Z is —CH=CH—, and comprises: steps (a) and (b), as shown above; in step (c) reacting the compound of formula (3) with a nucleophilic reagent of formula (4), wherein Z is —CH=CH—, and M and $R^5$ are as described above, to form the chiral compound of formula (5), wherein Z is —CH=CH—; and following with steps (d)–(g) as shown above to give the desired product.

A variant preferred embodiment of the process is that for preparing a chiral compound of formula (1), wherein Z is —CH=CH—and R is $C_1$–$C_6$-alkyl, and comprises: steps (a) and (b), as shown above; in step (c) reacting the compound of formula (3) with a nucleophilic reagent of formula (4), wherein Z is —CH=CH—, R is $C_1$–$C_6$-alkyl, and M and $R^5$ are as described above, to form the chiral compound of formula (5), wherein Z is —CH=CH—and R is $C_1$–$C_6$-alkyl; and following with steps (d)–(g) as shown above to give the desired product.

A compound prepared by this preferred embodiment immediately above is trans-(6aR,12bS)-10,11-dihydroxy-5,6,6a,7,8,12b-hexahydro-2-methylbenzo[a]-phenanthridine coupled with a pharmaceutically-acceptable salt.

The novel process, as described, refers to (2R)-starting materials, (2R)- and (5aR,11S)- or (6aR,12bS)-intermediate products, and final products of the (5aR,11S)- or (6aR,12bS)-configurations, which presently are the most desirable isomers. It will be obvious to those skilled in the art that if a racemic starting material is used, a racemic final product may be obtained. Likewise if a (2S)-starting material is used, the resulting final product will have the analogous (5aS,11 bR)- or (6aS,12bR)-configurations.

Non-critical conditions suitable for each of the several steps of the invention will be readily apparent to those skilled in the chemical arts. For example, step (a) commences with the protected-catechol-substituted chiral (substituted amino)butanoic acid compound (2). This compound can be made by reacting a chiral N-protected-D-aspartic anhydride with a protected catechol in the presence of $AlCl_3$, with nitromethane as the solvent, followed by reduction of the intermediate thus formed with a ketone reducing reagent. Similarly, formation of compound (5) utilizes an alkali metal or Grignard reagent. Both alkali metals and Grignard reagents are old and well known in the art, as are conditions suitable for their use.

Cyclizing of compound (6) to form the chiral trans-compound (7) involves the use of a Lewis Acid in a suitable solvent. Lewis Acids are defined below and suitable solvents therefor are generally known to those skilled in the art. Thus, suitable solvents for Lewis Acids are organic and generally aprotic and include, for example $CH_2Cl_2$, ethyl acetate and others. Since this is the step that produces the proper stereochemical arrangement of the compounds, it is important to select Lewis Acids and solvents that favor the desired configuration by a ratio of several fold. Applicants have generally found that $SnCl_4$ in $CH_2Cl_2$ produces the desired configuration in a ratio of about 4:1; $SnCl_4$ in ethyl acetate produces the desired configuration in a ratio of about 10:1; and $BF_3$ in ethyl acetate produces the desired configuration in a ratio of about 13:1.

The conditions appropriate for removing amino-protecting group $R^2$ are also well known in the art. See, for example, T. H. Greene and P. G. M. Wuts, *Protective Groups in Organic Synthesis*. 2nd edition, John Wiley & Sons, New York (1991).

Finally, the conditions for closing the chiral compound (7) to form the tetracyclic structure (8) are also known in the art. For example, depending on the substituent at $R^5$, these ring-closing reactions may include intramolecular alkylation or acylation of the amine and the Pictet-Spengler reaction.

It is further intended that the process will be carried out by skilled chemist who make changes, such as preferably, but not necessarily, carrying out sequential reactions in the same vessel, or changing solvents or reaction temperatures or equipment, especially in scaled-up reactions, and especially for economic reasons, and such modifications are considered to be within the scope of the present invention.

It will be obvious that the compounds produced by this process may easily be converted into a pharmaceutically-acceptable salt or pro-drug by standard methods known to those one skilled in the art.

An "alkali metal" is lithium, sodium or potassium.

"$C_1$–$C_6$-alkyl" means a straight- or branched-chain carbon radical of the size indicated, including, but not limited to methyl, ethyl, n-propyl, isopropyl, n-butyl, sec-butyl, isobutyl, t-butyl, pentyl, hexyl, and the like.

"Amino-protecting group" refers to a group used to derivatize amino nitrogen atoms in order to prevent undesired reactions or degradation during a synthesis. The term, "protecting group," is well known in the art and refers to substituents on functional groups of compounds undergoing chemical transformation which prevent undesired reactions and degradations during a synthesis; see, for example, T. H. Greene and P. G. M. Wuts, *Protective Groups in Organic Synthesis*, 2nd edition, John Wiley & Sons, New York (1991). Commonly-used amino-protecting groups include benzyloxycarbonyl, t-butyloxycarbonyl, trifluoroacetyl, and trimethylacetyl, and the like.

"Catechol-protecting groups" refers to groups used to derivatize catechol hydroxyl oxygen atoms in order to prevent undesired reactions or degradation during a synthesis (c.f., T. H. Greene, op. cit.). These derivatizing groups may be selected from phenol-protecting groups or they may be selected from those groups which are particularly suitable for the protection of catechols because of the proximity of the two hydroxyl functions on the catechol ring. Commonly used catechol-protecting groups include dimethyl ethers, dibenzyl ethers, cyclohexylidene ketals, methylene acetals, acetonide derivatives, diphenylmethylene ketals, cyclic borate esters, cyclic carbonate esters, cyclic carbamates, and the like.

The term, "hydroxamide-generating reagents," as used herein, refers to the combination of reagents necessary to produce a hydroxamide, such as, for example, N-methylmorpholine (NMM), followed by isobutyl chloroformate then dimethylhydroxylamine or oxazolidine in the presence of a moderately-strong base, such as sodium carbonate, for example (cf., Cupps, op. cit. and Nahm and Weinreb, *Tetrahedron Lett.*, 22:3815–3818 (1981)).

The term, "hydroxymethyl-equivalent group," as used herein, refers to a group which functions as a replacement for the hydroxymethyl group under the conditions of the reaction or may be converted to a hydroxymethyl group, for example —$CH_2$—O—Li, —$CH(OC_3)_2$, or —CO—N$(C_2H_5)_2$.

A "ketone reducing reagent" refers to reagents which will reduce the ketone group to a methylene group without affecting other reducible groups in the molecule, including, for example, H$_2$ over 10% Pd/C, H$_2$ over 5% Pt/C, triethylsilane in trifluoroacetic acid.

A "Lewis acid" is an aprotic electron pair acceptor including, but not limited, to such compounds as, for example, BCl$_3$, AlCl$_3$, SnCl$_4$ and BF$_3$.

"Pharmaceutically-acceptable salt(s)" refers to salt(s), well known in the art, which are, within the scope of sound medical judgment, suitable for use in contact with the tissues of humans and animals without undue toxicity, irritation, allergic response and the like, and are commensurate with a reasonable benefit/risk ratio, effective for the intended use thereof in the treatment of dopamine-related psychological, neurological, cardiovascular cognitive and addictive behavior disorders or substance abuse or addictive behavior. S. M. Berge et al describe pharmaceutically-acceptable salts in detail in *J. Pharmaceutical Sciences*, 66:1–19 (1977). These salts may be prepared in situ during the final isolation and purification of the compounds of formula (1), or separately by reacting the free base function with a suitable organic acid. Representative acid addition salts include hydrochloride, hydrobromide, sulfate, bisulfate, acetate, oxalate, valerate, oleate, palmitate, stearate, laurate, borate, benzoate, lactate, phosphate, toluenesulfonate, methanesulfonate, citrate, maleate, fumarate, succinate, tartrate, ascorbate, glucoheptonate, lactobionate, lauryl sulfate, and the like. Representative alkali or alkaline earth metal salts include sodium, calcium, potassium, magnesium, and the like.

The following examples are provided as illustration and not limitation of the novel process of the invention.

The following abbreviations are used: DMF for dimethylformamide; e.e. for enantiomeric excess, which is a measure of chiral purity; nBuLi for n-butyllithium; NMM for N-methylmorpholine; and THF for tetrahydrofuran.

EXAMPLE 1 trans-(5aR,11 bS)-4,5,5a,6,7,11b-hexahydro-2-propyl-3-thia-5-azacyclopenta[c]-phenanthrene-9,10-diol hydrobromide

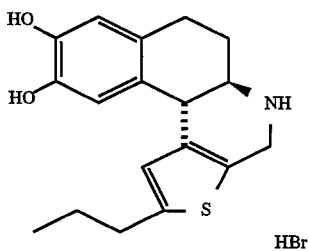

1a. (R)-(−)-4-(3,4-Dimethoxyhenyl)-4-oxo-2-((trifluoroacetyl)amino)butanoic Acid To AlCl$_3$ (248 g, 1.86 mole) cooled to −78° C. under nitrogen was added nitromethane (1000 mL). Veratrole (192.9 g, 1.40 mole) was then added carefully, while the internal temperature was kept below −30° C. The reaction mixture was warmed to −5° C., and the AlCl$_3$ dissolved in about 20 min. The mixture was cooled to −25° C. and N-trifluoroacetyl-D-aspartic anhydride (196.6 g, 931 mmole) was added. The reaction mixture was stirred at room temperature for 45 hr, carefully poured onto 4 kg of ice, and then vigorously stirred for 25 min. The mixture was then extracted with ethyl acetate (3×1000 mL), the combined ethyl acetate solution was concentrated under reduced pressure, and the residue was chased with toluene (2×600 mL) to remove residual nitromethane. The residue was redissolved in ethyl ether (1.5 L) and treated carefully with saturated aqueous solution of NaHCO$_3$ until pH of the aqueous solution reached 8. The ether solution was discarded, and the aqueous solution was chilled to ~5° C. by adding ice to it. The aqueous solution was then carefully acidified to pH 2 by adding 3N HCl. The aqueous solution was extracted with ethyl acetate (2×1000 mL), and the combined ethyl acetate solution was washed with H$_2$O (5×2000 mL) to remove any N-trifluoroacetyl-D-aspartic acid by-product. The washed organic solution was dried (MgSO$_4$), filtered and concentrated under reduced pressure to an oil which was left under high vacuum overnight to give a brown glassy solid (237 g, 73% yield). NMR(CDCl$_3$/DMSO-d$_6$) δ: 3.58 (dd, J=18,3 Hz, 1H), 3.82 (dd, J=18,3 Hz, 1H), 3.94 (s, 3H), 3.97 (s, 3H), 4.88 (q, J=3 Hz, 1H), 6.91 (d, J=7.5 Hz, 1H ), 4.49 (d, J=2 Hz, 1H), 7.58 (dd, J=7.5, 2 Hz, 1H), 7.75 (broad d, J=7.5 Hz, 1H). The purity of this material was estimated to be 95%, based upon the NMR spectrum, and it was used directly for next step without further purification.

1b. (R)-(−)-4-(3,4-Dimethoxyphenyl)-2-((trifluoroacetyl) amino)butanoic Acid.

A mixture of (R)-(−)-4-(3,4-dimethoxyphenyl)-4-oxo-2-((trifluoroacetyl)amino)butanoic acid (from step 1a above, 237 g, 678.6 mmole), 10% Pd/C (23.7 g) and concentrated HCl (115 mL) in 900 mL of isopropyl alcohol was hydrogenated under 4 atm hydrogen at room temperature for 14 hr. After filtration, ethyl ether (2 L) was added to the filtrate and the resultant solution was washed with water (4×1.5 L). The organic solution was evaporated under reduced pressure to leave an oily residue, which was redissolved in ethyl ether (700 mL) and treated with saturated aqueous NaHCO$_3$ until pH 8 was reached. The aqueous solution was separated, washed with ether (2×500 mL) and then chilled to ~5° C. by adding ice to it. After careful acidification to pH 2 by addition of 6N HCl, the mixture was extracted with ether/THF (10:1, 2×1 L). The organic layers were combined, dried (MgSO$_4$), filtered and concentrated under reduced pressure to give a light brown semi-solid which was recrystallized from hexane/EtOAc solvent system. The title compound was obtained as a white crystalline solid and was collected by filtration (102.33 g, 45% yield). mp 159°–160° C.; NMR(CDCl$_3$) δ: 2.05–2.35 (m, 2H), 2.65 (t, J=7.5 Hz, 2H), 3.70 (s, 3H), 3.80 (s, 3H), 4.60 (broad q, J=7.5 Hz, 1H), 6.70–6.81 (m, 3H), 7.19 (broad d, J=7.5 Hz, 1H). [α]$_D$-6.44 (c 1.35, MeOH).

1c. (.2R)-N-methoxy-N-methyl-4-(3,4-dimethoxyphenyl)-2-((trifluoroacetyl)-amino)butanamide To a solution of (R)-(−)-4-(3,4-dimethoxyphenyl)-2-[(trifluoroacetyl)amino]-butyric acid (8 g, 24 mmol, prepared according to step 1b above) in 65 mL of THF was added N-methylmorpholine, (2.6 mL, 24 mmol), and the solution was cooled to −25° C. and stirred for 30 min. Isobutylchloroformate (3.1 mL, 24 mmol) was then added, and the solution was stirred for 1.5 minutes. To this solution was added an alkaline solution of dimethylhydroxylamine (prepared by adding dimethylhydroxylamine hydrochloride, (3.5 g, 36 mmol) to a solution of 24 mL of THF and 1 mL of water, adding K$_2$CO$_3$, (7 g, 216 mmol), and stirring for 30 min, and filtering), and the reaction mixture was stirred for 30 min at −25° C. The mixture was diluted with 200 mL of ethyl acetate, and the organic layer was separated and washed with 50 mL each of water, 1N NaOH, 1N HCl, water and saturated NaCl. The organic layer was then dried over MgSO$_4$, filtered and evaporated to yield a colorless oil. The oil was crystallized from ether/hexanes to yield 7 g of the title compound (77%). mp 70°–72° C. MS: 379 (M+H)$^+$, 396 (M+NH$_4$)$^+$. NMR (CDCl$_3$) δ: 2.02 (m, 1H), 2.15 (m, 1H), 2.63 (m, 2H), 3.21 (s, 3H), 3.65 (s, 3H), 3.86 (s, 3H), 3.89 (s, 3H), 5.01 (m, 1H), 6.70–6.85 (m, 3H), 7.11 (s, 1H). [α]$_D$=−8.87° (c=1.42, CH$_2$Cl$_2$).

1d. 1-(4-Bromo-2-thienyl)-1-propanone

A 47.3 g (338 mmol) sample of 1-(2-thienyl)-1-propanone (Aldrich) was dissolved in 225 mL of CHCl$_3$ and 101.3 g (760 mmol) of AlCl$_3$ was added with stirring. To this mixture was added a solution of bromine (57.5 g, 360 mmol) in 375 mL of CHCl$_3$. The mixture was stirred at room temperature over night then poured into 500 mL of ice water. The organic layer was separated, washed with water (2×200 mL), dried over MgSO$_4$, filtered and evaporated to yield 81 g of the crude title compound, which was taken directly to the next step. mp 40°–41° C.; MS: 158 (M+H)$^+$, 236 (M+NH$_4$)$^+$; NMR (CDCl$_3$) δ: 1.22 (t, 3H, J=7.5 Hz), 2.91 (q, 2H, J=7.5Hz), 7.51 (d, 1H), 7.60 (d, 1H). IR (KBr): 2960, 1670, 1400, 1220 cm$^{-1}$.

1e. 4-Bromo-2-propylthiophene

To a solution of crude 1-(4-bromo-2-thienyl)-1-propanone, (53 g, 242 mmol, from step 1d above) in 210 mL of ethylene glycol was added hydrazine monohydrate (30 mL, 617 mmol). The resulting solution was then heated to 160° C. with stirring for 45 min. The solution was cooled to 35° C. and 42 g of KOH (750 mmol) was added. The mixture was heated to 160° C. and stirred for 1.5 hr. The reaction was cooled to room temperature, and 450 mL of water was added. The mixture was then acidified with conc. HCl, and the product was extracted with pentane (3×200mL). The pentane was dried over MgSO$_4$, filtered and evaporated to yield 39.7 g of crude product as a free flowing oil. The material was purified by flash chromatography on silica gel, eluting with pentane, to afford 27 g, (54% yield) of the title product. b.p. 120°–125° C. @7 mm Hg. NMR (CDCl$_3$) δ: 0.97 (t, 3H, J=7.5 Hz), 1.69 (sextet, 2H, J=7.5 Hz), 2.75 (t, 2H, J=7.5 Hz), 6.70 (d, 1H), 7.00 (d, 1H).

1f. (2R)-4-(3,4-Dimethoxyphenyl)-1-(2-propyl-4-thienyl)-2-(trifluoroacetyl) amino-1-butanone A sample of 4-bromo-2-propylthiophene (17.4 g, 85 mmol, from step 1e above) was dissolved in 200 mL of ether and cooled to −78° C. To this solution was added 38 mL of 2.5M nBuLi in hexanes (Aldrich), maintaining the reaction temperature at less than −70° C. The reaction was stirred at −78° C. for 30 min, and a pre-cooled (−78° C.) solution of (2R)-N-methoxy-N-methyl-4-(3,4-dimethoxyphenyl)-2-((trifluoroacetyl)amino)butanamide (10.7 g, 28.3 mmol, from step 1a above) in 50 mL of THF was added at such a rate to maintain the reaction temperature at less than −70° C. The reaction was quenched with sat. NH$_4$Cl, stirred at room temperature and diluted with 300 mL of ethyl acetate. The organic layer was separated and washed with 1N HCl, sat. NaCl and dried over MgSO$_4$, then filtered and evaporated to yield the crude product as an oil, (12.5 g), which was taken directly to the next step. MS: 444 (M+H)$^+$, 461 (M+NH$_4$)$^+$. NMR (CDCl$_3$) δ: 0.98 (t, 3H), 1.68 (m, 2H), 2.04 (m, 1H), 2.30 (m, 1H), 2.63 (dt, 2H, J=2.4 Hz, 7.5 Hz), 2.75 (t, 2H), 3.87 (s, 3H), 3.88 (s, 3H), 5.37 (dt, 1H, J=3 Hz, 7.5 Hz), 6.74 (m, 2H), 6.81 (d, 1H), 7.05 (bs, 1H), 7.31 (bd, 1H), 7.72 (d, 1H); [α]$_D$=−38° (c=0.75, CHCl$_3$).

1g. alternate preparation of (2R)-4-(3,4-Dimethoxyphenyl)-1-(2-propyl-4-thienyl)-2-(trifluoroacetyl)amino-1-butanone A flask equipped with N$_2$ inlet, magnetic stirrer and addition funnel was charged with Mg turnings (2.25 g, 92.57 mmol), 4-bromo-2-propylthiophene (17.35 g, 84.63 mmol, from step 1e above) and THF, and the suspension was stirred at room temperature for 1 hr. The reaction mixture was cooled by immersion in an ice bath (20 min.) and the compound from step 1a above (10.0 g, 26.45 mmol) in THF (40 mL) was added dropwise. The orange reaction mixture was stirred at 0° C. for 10 min, then warmed to room temperature and stirred an additional 10 min. The reaction was quenched by addition of satd. NH$_4$Cl (50 mL), stirred for 5 min, then partitioned between EtOAc/water (1:1; 100 mL). The organic layer was removed, and the aq. was extracted with EtOAc (1×75 mL). The combined organic extracts were dried over Na$_2$SO$_4$ and concentrated to afford 16.4 g of a dark orange oil. The crude product was subjected to column chromatography on silica gel, eluting with 20% EtOAc/hexane to yield 10.98 g (94%) of the title product as a pale orange oil. The physical and spectral data corresponded to that in step 1f above.

1h. (2R)-4-(3,4-Dimethoxyphenyl)-1-(2-propyl-4-thienyl)-2-(trifluoroacetyl) amino-1-butanol To a solution of the ketone from step 1f or 1g above (12.5 g, 28.8 mmol) in 300 mL of absolute ethanol cooled to 0° C. was added 1.4 g (36 mmol) of NaBH$_4$, and the reaction was stirred at room temperature for 2 hr. The reaction was quenched with 1N HCl and diluted with ethyl acetate. The organic layer was separated and washed with water (2×100 mL), sat. NaCl, dried over MgSO$_4$, then filtered and evaporated to a solid. The solid was triturated with 5:1 hexanes/ethyl acetate to yield pure title product as a 4:1 mixture of trans:cis product (7.65 g). NMR (CDCl$_3$) δ: 0.95 (t, 3/5H, J=7.5 Hz), 0.97 (t, 3H, J=7.5 Hz), 1.52–1.92 (m, 4 4/5H), 2.42–2.70 (m, 2 2/5H), 2.74 (t, 2/5H, J=7.5 Hz), 2.75 (t, 2H, J=7.5 Hz), 3.75 (m, 1H), 3.77 (m, 1/5H), 3.84 (s, 3H), 3.85 (s, 3H), 3.87 (s, 3/5H), 3.88 (s, 3/5H), 4.85 (d, 1/5H, J=3 Hz), 4.90 (d, 1H, J=3 Hz), 6.42 (bd, 1H), 6.51 (bd, 1/5H), 6.63 (m, 3 3/5H), 6.70–6.82 (m, 1 1/5H), 6.95 (s, 1/5H), 6.97 (s, 1H); MS 445 (M+H)$^+$, 463 (M+NH$_4$)$^+$.

1i. trans -(1S,2 R)-N-Trifluoroacetyl-6,7-dimethoxy-1,2,3,4-tetrahydro-1-(2-propyl-4-thienyl)-2-naphthylamine To a solution of the alcohol from step 1h above (7.65 g, 17 mmol) in 200 mL of ethyl acetate cooled to 0° C. was added 17 mL of 1M SnCl$_4$ in CH$_2$Cl$_2$. The reaction was stirred at room temperature for 16 hr. The reaction was quenched with water, and the organic layer was separated, washed with water and sat. NaCl, dried over MgSO$_4$, filtered and evaporated to a solid. The solid was recrystallized from one part ethyl acetate and five parts hexanes to yield the trans title product as a white crystalline solid, (5.9 g, 83% yield). mp 157°–158° C. NMR (CDCl$_3$) δ: 0.95 (t, 3H, J=7.5 Hz), 1.66 (m, 2H), 1.88 (m, 1H), 2.10 (m, 1H), 2.72 (t, 2H, J=7.5 Hz), 2.81 (t, 1H), 2.92 (m, 1H), 3.74 (s, 3H), 3.89 (s, 3H), 4.01 (d, 1H, J=6 Hz), 4.39 (dt, 1H, J=3 Hz, 7.5 Hz), 6.28 (bd, 1H), 6.45 (s, 1H), 6.53 (s, 1H), 6.59 (s, 1H), 6.65 (s, 1H); MS 428 (M+H)$^+$, 445 (M+NH$_4$)$^+$. [α]$_D$=−18.6° (c=0.05, CH$_2$Cl$_2$).

1j. trans-(1S,2R)-6,7-Dimethoxy-1,2,3,4-tetrahydro-1-(2-propyl-4-thienyl)-2-naphthylamine To a solution of (R)-N-trifluoroacetyl-6,7-dimethoxy-1,2,3,4-tetrahydro-1-(2-propyl-4-thienyl)-2-naphthylamine (5.9 g, 13.3 mmol, from step 1i above) in 200 mL of 10% aqueous methanol was added 11.8 g of K$_2$CO$_3$, (80 mmol). The resulting suspension was heated at reflux for two hours, then cooled to room temperature and diluted with ethyl acetate. The organic layer was washed with water (2×100 mL) and sat. NaCl, dried over MgSO$_4$, filtered and evaporated to yield the title compound as an amorphous solid (4.4g, 100% yield). The compound was taken to the next step without further purification. MS: 332 (M+H)$^+$, 349 (M+NH$_4$)$^+$. NMR (CDCl$_3$) δ: 0.93 (t, 3H, J=7.5 Hz), 1.59–1.79 (m, 3H), 2.06 (m, 1H), 2.73 (t, 2H, J=7.5 Hz), 2.89 (m, 2H), 3.15 (m, 1H), 3.64 (s, 3H), 3.70 (d, 1H, J=9

Hz), 3.86 (s, 3H), 6.32 (s, 1H), 6.48 (s, 1H), 6.60 (s, 1H), 6.88 (d, 1H). 1k. trans -(5aR,11 bS)-9.10-dimethoxy-4,5,5a, 6,7,11 b-hexahydro-2-propyl-3-thia-5-aza-cyclopenta[c] phenanthrene hydrochloride To a solution of the amine compound from step 1j above (4.4 g, 13.3 mmol) in 100 mL of absolute ethanol was added 37% formaldehyde in water (10.3 mL, 133 mmol). The reaction was stirred at room temperature for 15 min, then 3.7 mL of conc. HCl was added and the reaction was heated at reflux for 4 hr. The reaction was then cooled, and the suspension was diluted with 200 mL of ether and stirred at room temperature for 1 hr. The mixture was filtered, and the product was dried to yield 4.5 g of a white crystalline solid. mp 284°–286° C. (dec); NMR (CDCl$_3$) δ: 1.00 (t, 3H, J=7.5 Hz), 1.69 (m, 3H), 2.39 (m, 1H), 2.62 (m, 1H), 2.79 (t, 2H, J=7.5 Hz), 2.84–3.09 (m, 2H), 3.18 (m, 1H), 3.83 (s, 3H), 388 (s, 3H), 4.30 (d, 1H, J=10.5 Hz), 4.37 (d, 1H, J=16.5 Hz), 4.54 (d, 1H, J=15 Hz), 6.70 (s, 1H), 6.92 (s, 1H), 7.01 (s, 1H); MS: 344 (M+H)$^+$, 361 (M+NH$_4$)$^+$. [α]$_D$=−263.14° (c=3.31, methanol). Free base: [α]$_D$=343° (c=0.52, methanol).

1l. trans -(5aR,11 bS)-4,5,5a,6,7,11 b-hexahydro-2-propyl-3-thia-5-azacyclo-penta[c]phenanthrene-9,10-diol hydrobromide A 3-neck flask equipped with a mechanical stirrer and a thermometer was charged with a suspension of trans -(5aR, 11 bS)-9,10-dimethoxy-4,5,5a,6,7,11 b-hexahydro-2-propyl-3-thia-5-aza-cyclopenta[c]phenanthrene hydrochloride (19.22 g, 50.6 mmol, from step 1k above) in methylene chloride (750 mL), then placed in a dry ice bath. BBr$_3$ (210 mL, 1.0M solution in CH$_2$Cl$_2$, 210 mmol), was added via syringe over a period of 20 minutes, resulting in a clear light brown solution. The reaction mixture was stirred at −70° C. (internal temperature) for 45 minutes, then placed in an ice bath and stirred for an additional 2 hr. The reaction mixture was recooled to −78° C. and carefully quenched with 180 mL of MeOH, added dropwise. The cooling bath was removed and the reaction was stirred at room temperature for 1.5 hr. The reaction mixture was concentrated in vacuo from methanol, CH$_2$Cl$_2$-ether to afford the title product as a tan solid. The product was dried under high vacuum for 16 hr to afford 20.9 g. The compound was >99% pure by HPLC on a reverse phase C-60 Dynamax column using a 1 to 1 mixture of methanol and 0.1% trifluoroacetic acid as the mobile phase (UV detector at 254 nm). mp 155°–162° C. (dec). MS :316 (M+H)$^+$. NMR (CDCl$_3$) δ: 1.03 (t, 3H, J=8 Hz), 1.75 (sx, 2H, J=8 Hz), 1.9–2.0 (m, 1H), 2.28–2.41 (m, 1H), 2.87 (t, 2H, J=8 Hz), 2.88–3.05 (m, 2H), 3.15–3.27 (m, 1H), 4.02 (d, 1H, J=11 Hz), 4.46 (s, 2H), 6.6 7 (s, 1H), 6.90 (s, 1H), 7.02 (s, 1H). Anal. calc. for C$_{18}$H$_{22}$BrNO$_2$S.0.7H$_2$O: C, 52.87;H, 5.77; N, 3.43; found: C, 52.87; H, 5.45; N, 3.34. [α]$_D$=−167° (c=1.03, methanol). Total overall yield from the (2R)-4-(3,4-dimethoxyphenyl) -2-((trifluoroacetyl)amino)- butyric acid starting material was 48% for the chiral product.

EXAMPLE 2 trans-(6aR. 12bS)-10,11-dihydroxy-5,6,6a,7,8,12b-hexahydro-2-methyl-benzo[a]-phenanthridine hydrobromide.

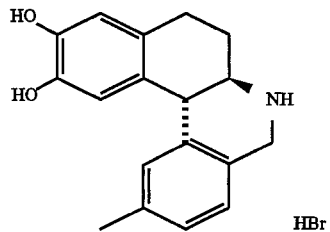

2a. (2R)-4-(3,4-dimethoxyphenyl)-1-(3-methylphenyl)-2-((trifluoroacetyl)amino)butanone The title compound was prepared, using the procedures described in example 1f, substituting 3-bromotoluene (Aldrich Chemical Co) for 4-bromo-2-propylthiophene. (86% yield) m.p. 62°–64° C. MS m/z 427(M+NH$_4$)$^+$. IR (KBr): 3280, 1720, 1680, 1518, 1150 cm$^{-1}$. $^1$H NMR (CDCl$_3$, 300 MHz) δ: 2.02 (m, 1H), 2.30 (m, 1H), 2.37 (s, 3H), 2.62 (t, J=7.5 Hz, 2H), 3.84 (s, 3H), 3.87 (s, 3H), 5.62 (dt, J=3, 7.5 Hz,1H), 6.71 (s, 2H), 6.80 (d, 1H), 7.43 (m, 2H), 7.55 (s, 3H), 7.61 (d, J=8 Hz, 1H). Analysis calculated for C$_{21}$H$_{22}$NO$_4$F$_3$: C: 61.61; H:5.42; N: 3.42. Found: C: 61.40; H: 5.40; N: 3.33. [α]$_D$$^{25}$=−5.04 (c0.5, CH$_2$Cl$_2$).

2b. trans-(1S,2R)-1-(3-methylphenyl)-1,2,3,4-tetrahydro-6, 7-dimethoxy-N-trifluoroacetyl-2-naphthaleneamine The title compound was prepared from the compound of step 2a using the procedures described in example 1h and 1i. (58% yield) m.p. 164°–166° C. MS m/z 411 (M+NH$_4$)$^+$. IR (KBr): 3320, 1685, 1510, 1180 cm$^{-1}$. $^1$H NMR (CDCl$_3$, 300 MHz) δ: 1.87 (m, 1H), 2.06 (m, 1H), 2.31 (s, 3H), 2.84 (m, 1H), 2.95 (m, 1H), 3.69 (s, 3H), 3.90 (s, 3H), 4.02 (d, J=6 Hz,1H), 4.36 (m, 1H), 6.30 (bs, 1H), 6.35 (s, 1H), 6.67 (s, 1H), 6.82 (d, J=8 Hz, 1H), 6.91 (s,1H), 7.05 (J=8 Hz, 1H), 7.18 (t, J=8 Hz, 1H). Analysis calculated for C$_{21}$H$_{22}$NO$_3$F$_3$.0.2 H$_2$O: C: 63.53; H: 5.69; N: 3.53. Found: C: 63.26; H: 5.70; N: 3.47. [α]$_D$$^{25}$32 −46.0 (c 0.5, CH$_2$Cl$_2$).

2c. trans-(1S,2R)-1-(3-methylphenyl)-1,2,3,4-tetrahydro-6, 7-dimethoxy-2-naphthaleneamine The title compound was prepared from the compound of step 2c using the procedure described in example 1j. (97% yield) m.p. 112°–114° C. MS m/z 298 (M+H)$^+$, 315(M+NH$_4$)$^+$. IR (KBr): 3440, 2920, 1510, 1250, 1110 cm$^{-1}$. $^1$H NMR (CDCl$_3$, 300 MHz) δ: 1.74 (m, 1H), 2.05 (m, 1H), 2.33 (s, 3H), 2.91 (m, 2H), 3.18 (m, 1H), 3.60 (s, 3H),3.64 (d, J=9 Hz, 2H), 3.88(s, 3H), 6.20 (s, 1H), 6.63 (s, 1H), 6.98 (m, 2H), 7.07 (d, J=8 Hz, 1H), 7.22 (t, J=8 Hz, 1 H). Analysis calculated for C$_{19}$H$_{23}$NO$_2$.0.3H$_2$O: C: 75.37; H:7.86; N: 4.63. Found: C: 75.27; H: 7.59; N: 4.46. [α]$_D$$^{25}$=−7.69 (c 0.13, CH$_2$Cl$_2$)

2d. trans-(6aR,12bS)-10,11-dimethoxy-5,6,6a,7,8,12b-hexahydro-2-methyl-benzo[a]phenanthridine A solution of the amine from step 2c (0.18g, 0.6 mmol) in ethanol (5 mL) was treated with K$_2$CO$_3$ (0.52 g, 3.6 mmol), stirred for 10 minutes at room temperature, then treated with paraformaldehyde (0.04 g, 1.2 mmol) and allowed to stir overnight. The suspension obtained was then filtered. The filtrate was concentrated under reduced pressure then dissolved in trifluoroacetic acid (5 mL). The resulting mixture was refluxed overnight, then concentrated. The residue was partitioned between ethyl acetate and sat. aq. NaHCO$_3$. The organic extract was washed with water, brine, dried and concentrated. The residue was purified via silica gel column chromatography eluting with 98:2:0.5 CH$_2$Cl$_2$: MeOH: NH$_4$OH to give 0.14 g (79% yield) of the title compound. m.p. 138°–140 ° C. MS m/z 310 (M+H)$^+$. IR (KBr): 3440, 2840, 1510, 1230 cm$^{-1}$. $^1$H NMR (CDCl$_3$, 300 MHz) δ1.71 (m, 1H), 2.18 (m, 1H), 2.36 (s, 3H), 2.70 (m, 1H), 2.84 (m, 1H), 2.90 (m,1H), 3.78 (s, 3H), 3.82 (s, 1H), 3.89 (s,3H), 4.07 (s, 2H), 6.75 (s, 1H), 6.94 (s, 1H), 7.05 (s, 1H), 7.06 (s, 1H), 7.30 (s,1H). Analysis calculated for $C_{20}H_{23}NO_2 \cdot 0.3H_2O$: C: 76.31; H:7.56; N: 4.45. Found: C: 76.42; H: 7.36; N: 4.31. $[\alpha]_D^{25}$=−208.4 (c0.5, $CH_2Cl_2$).

2e. trans-(6aR, 12bS)-10,11-dihydroxy-5,6,6a,7,8,12b-hexahydro-2-methylbenzo[a]phenanthridine hydrobromide The title compound was prepared from the compound of step 2e using the procedure described in example 11. (86% yield) m.p. 242°–244 ° C. MS m/z 282 (M+H)⁺. IR (KBr): 3400, 2920, 1620, 1520 cm⁻¹. ¹H NMR ($CD_3OD$, 300 MHz) δ1.90 (m, 1H), 2.24 (m, 1H), 2.33 (s, 3H), 2.81 (m, 2H), 2.94 (m, 1H), 4.12 (d,J=11.5 Hz, 1H), 4.35 (s, 2H), 6.63 (s, 1H), 6.77 (s, 1H), 7.15 (d,J=8 Hz, 1H), 7.22 (d, J=8 Hz, 1H), 7.28 (s, 1H). Analysis calculated for $C_{18}H_{20}BrNO_2 \cdot 0.1$ HBr: C: 47.91; H:4.71; N: 3.10. Found: C: 48.19; H: 5.02; N: 2.90.

EXAMPLE 3–6

Alternate preparations of (R)-(−)-4-(3,4-Dimethoxyphenyl)-2-((trifluoroacetyl)amino)butanoic Acid.

Competitive Binding

D-1 and D-2 Receptor Binding Assays

Homogenized rat caudate was incubated in the presence of [¹²⁵I]SCH-23982 (a selective antagonist of the dopamine D-1 receptor) and the compounds of this invention, according to procedures described by A. Sidhu, et at. in European I *Pharmacology*, 113:437 (1985) and in *European I Pharmacology*, 128:213 (1986). The compounds compete with the radiolabeled ligand for occupancy of the receptors and the molar potency of each compound was quantified. The affinity of the compound for the receptor (Ki) was calculated as described by Y. C. Cheng and W. H. Prusoff in *Biochemical Pharmacology*, 22:3099 (1973) from the relationship $Ki=IC_{50}(1+[L]/K_D)$ where $IC_{50}$ is the concentration of test compound which produces a 50% inhibition in the specific binding of the radioligand, L; [L]is the concentration of radioligand; and $K_D$ is the affinity of the radioligand for the receptor.

The procedure for the dopamine D-2 receptor binding assay was similar to that used for the D-1 receptor assay. Homogenized rat caudate was the source of the D-2 receptors. The tissue homogenate was incubated in the presence of [³H]-spiroperidol (a selective antagonist of the dopamine D-2 receptor) and the compounds being evaluated, according to the protocol described by T. Agui, N. Amlaiky, M. G. Caron and J. W. Kebabian in *Molecular Pharmacology*, 33:163 (1988). The molar affinity of the compound for the receptor binding site was calculated by the same method used for the D-1 receptor assay, assuming a competitive interaction between the compound and the radiolabeled ligand.

The competitive binding data (Ki values) from the D-1 and D-2 receptor binding assays are shown in Table 1. The Ki values are inversely proportional to the affinity of the compound for the receptor.

TABLE 1

Competitive Binding for D-1 and D-2 Receptors

| Example Number | D-1 Ki (mM) | D-2 Ki (mM) |
| --- | --- | --- |
| dopamine | 8.0 | 6.3 |
| 1 | 0.018 | 0.16 |
| 2 | 0.045 | 0.83 |

TABLE 1-continued

Competitive Binding for D-1 and D-2 Receptors

| Example Number | D-1 Ki (mM) | D-2 Ki (mM) |
| --- | --- | --- |
| 3 | 0.006 | 0.64 |
| 4 | 0.002 | 0.34 |
| 5 | 0.018 | 1.4 |
| 6 | 0.051 | 3.3 |
| 7 | 0.02 | 1.7 |
| 8 | 0.094 | 3.0 |
| 9 | 0.051 | 2.3 |
| 10 | 0.56 | 4.6 |
| 11 | 0.15 | 3.1 |
| 12 | 1.0 | 10 |
| 13 | 0.077 | 0.91 |
| 14 | 0.008 | 0.14 |
| 15 | 0.013 | 0.15 |
| 16 | 0.022 | 0.45 |
| 17 | 0.16 | 1.5 |
| 18 | 0.060 | 0.52 |
| 19 | 0.36 | 0.75 |
| 20 | 0.008 | 0.29 |
| 21 | 0.015 | 0.066 |
| 22 | 0.012 | 0.66 |
| 23 | 0.006 | 0.29 |
| 24 | 0.006 | 1.27 |
| 25 | 0.073 | 1.31 |
| 27 | 0.011 | 0.21 |
| 29 | 0.006 | 0.29 |
| 30 | 0.062 | 0.56 |
| 31 | 0.687 | 0.54 |
| 32 | 0.004 | 0.13 |
| 33 | 0.282 | 0.56 |
| 34 | 0.004 | 0.42 |
| 35 | 0.440 | 1.76 |
| 36 | 0.517 | 2.08 |
| 37 | 0.710 | 3.19 |
| 38 | 1.43 | 2.58 |
| 39 | 0.45 | 1.62 |
| 40 | 0.015 | 0.48 |
| 41 | 0.021 | 0.60 |
| 42 | 0.453 | 0.64 |
| 43 | 0.028 | 0.12 |
| 44 | 0.025 | 0.38 |
| 45 | >2.5 | >5.0 |
| 46 | >5.0 | >5.0 |
| 47 | >10.0 | >5.0 |

Steps a and b of Example 1 above were repeated with varying amounts of veratrole (V), N-trifluoroacetyl-D-aspartic anhydride (NTAA), and $AlCl_3$, and the yields of product were obtained as reported in Table 1 below.

TABLE 1

Yields from Examples 3–6

| | | $AlCl_3$ in $CH_3NO_2$ | | |
| Example | V (mmol) | NTAA (mmol) | moles | Molarity | %yield |
| --- | --- | --- | --- | --- | --- |
| 3 | 0.008 | 0.09 | 0.175 | 0.7 | 61 |
| 4 | 0.145 | 0.173 | 0.345 | 0.7 | 69 |
| 5 | 0.340 | 0.227 | 0.457 | 1.07 | 89 |
| 6 | 1.396 | 0.931 | 1.859 | 1.859 | 73 |

EXAMPLES 7–9

Replicate preparations of (R)-(−)-4-(3,4-Dimethoxyphenyl)-2-((trifluoro-acetyl) amino)butanoic Acid. according to the method of Nordlander et al (op. cit.)

Steps a and b of Example 1 above were repeated, except using only methylene chloride as the solvent, as described by Nordlander et al with varying amounts of veratrole (V) and N-trifluoroacetyl-D-aspartic anhydride (NTAA), and AlCl₃, and the yields of product were obtained as reported in Table 2 below.

TABLE 2

Yields from Examples 7–9

| Example | V (mmol) | NTAA (mmol) | AlCl₃ moles | % yield |
|---|---|---|---|---|
| 7 | 0.005 | 0.033 | 0.083 | 7 |
| 8 | 0.165 | 0.100 | 0.265 | 5 |
| 9 | 0.287 | 0.174 | 0.465 | 9 |

What is claimed is:

1. A process for the preparation of a chiral compound of formula (1),

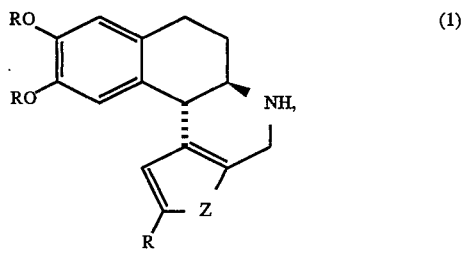

wherein R is hydrogen or a $C_1$–$C_6$-alkyl group, and Z is oxygen, sulfur or —CH=CH—, by:

(a) reacting a chiral starting material of formula (2),

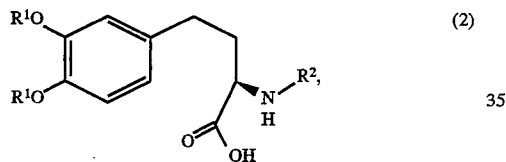

wherein $R^1$ is a catechol-protecting group and $R^2$ is an amino-protecting group, at −25° C. with N-methylmorpholine and isobutylchloroformate followed by reaction with dimethylhydroxylamine, to give the chiral intermediate compound of formula (3),

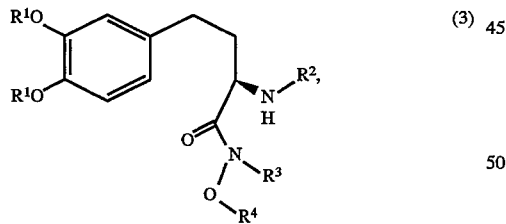

wherein $R^1$ and $R^2$ are as defined above and $R^3$ and $R^4$ are each methyl, or $R^3$ and $R^4$ taken together is —CH₂—CH₂—CH₂—, and isolating the compound of formula (3);

(b) reacting the compound of formula (3) with a nucleophilic reagent of formula (4),

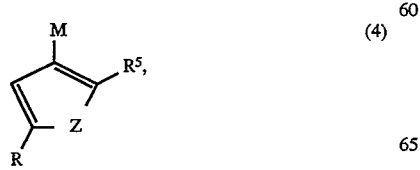

wherein R and Z are as described above, M is an alkali metal or the Grignard (MgX) moiety, and $R^5$ is hydrogen, hydroxymethyl, —CH₂—O—Li, —CH(OCH₃)₂, or —CO—N(C₂H₅)₂, to form the chiral compound of formula (5),

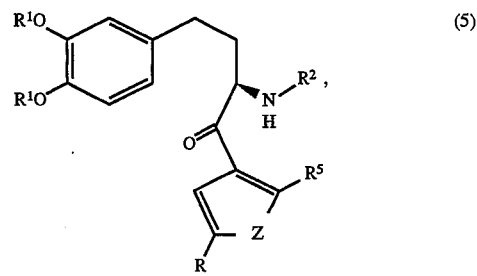

wherein R, $R^1$, $R^2$, $R^5$ and Z are as defined above, and isolating the compound of formula (5);

(c) reducing the compound of formula (5) with NaBH₄ at from 0° C. to room temperature to give the chiral compound of formula (6),

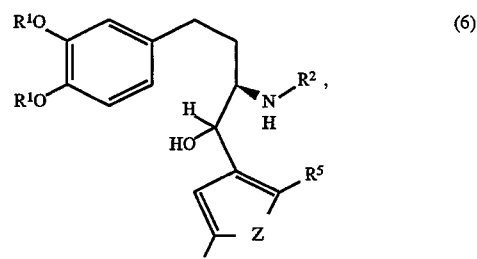

wherein R, $R^1$, $R^2$, $R^5$ and Z are as described above, and isolating the compound of formula (6);

(d) cyclizing the compound of formula (6) in the presence of a Lewis acid and methylene chloride or ethyl acetate to give a high yield of the chiral trans compound of formula (7),

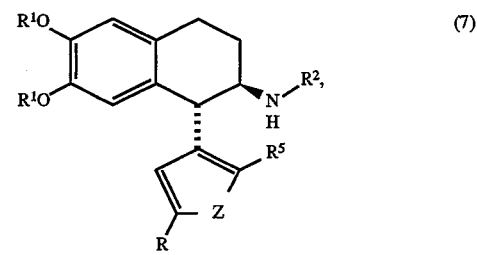

wherein R, $R^1$, $R^2$, $R^5$ and Z are as described above; and isolating the compound of formula (7);

(e) removing the $R^2$ and cyclizing the compound of formula (7), by reaction with formaldehyde in absolute ethanol then heating at reflux with conc. HCl, or by reaction with paraformadehyde in the presence of K₂CO₃ then heating at reflux with trifluoroacetic acid, to give the chiral intermediate of formula (8),

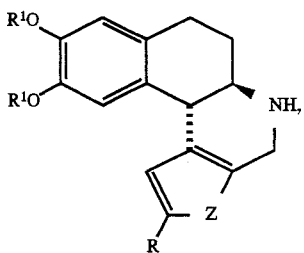

wherein R, R¹ and R² are as described above; isolating the compound of formula (8); and (f) deprotecting the protected-catechol groups R¹ of the compound of formula (8) and isolating the desired product (1), in high yield.

2. The process according to claim 1, wherein Z is sulfur.

3. The process according to claim 2, wherein R is propyl.

4. The process according to claim 3, wherein the product is trans-(5aR,11 bS)-4,5,5a,6,7,11 b-hexahydro-2-propyl-3-thia-5-aza-cyclopent-1-ena[c]phenanthrene-9,10-diol pharmaceutically-acceptable salt.

5. The process according to claim 1, wherein Z is —CH=CH—.

6. The process according to claim 5, wherein R is methyl.

7. The process according to claim 6, wherein the product is trans-(6aR,12bS)-10,11-dihydroxy-5,6,6a,7,8,12b-hexahydro-2-methyl-benzo[a]phenanthridine pharmaceutically-acceptable salt.

8. The process according to claim 1, wherein the solvent is ethylacetate and the Lewis acid is Boron trifluoride or SnCl₄.

* * * * *

UNITED STATES PATENT AND TRADEMARK OFFICE
CERTIFICATE OF CORRECTION

PATENT NO. : 5,659,037
DATED : August 19, 1997
INVENTOR(S) : P. P. Ehrlich et al.

It is certified that error appears in the above-identified patent and that said Letters Patent is hereby corrected as shown below:

```
Title page;
```

In the list of inventors, change "Chi-Nung Hsaio" to --Chi-Nung Hsiao--.

Signed and Sealed this

Twenty-second Day of September, 1998

Attest:

BRUCE LEHMAN

*Attesting Officer*  *Commissioner of Patents and Trademarks*